United States Patent [19]

Lu et al.

[11] Patent Number: 4,796,622

[45] Date of Patent: Jan. 10, 1989

[54] CATHETER WITH OXYHYDROGEN CATALYTIC THERMAL TIP

[75] Inventors: David Y. Lu, Rockville; Robert L. Bowman, Bethesda, both of Md.

[73] Assignee: The United States of America as represented by the Department of Health and Human Services, Washington, D.C.

[21] Appl. No.: 26,540

[22] Filed: Mar. 6, 1987

[51] Int. Cl.$^4$ ............................................. A61B 17/36
[52] U.S. Cl. ................................................ 128/303.1
[58] Field of Search ........ 128/303.1, 303.12, 395–398;
126/91 R, 91 A; 431/215, 268, 328

[56] References Cited

U.S. PATENT DOCUMENTS

| | | | |
|---|---|---|---|
| 2,764,969 | 10/1956 | Weiss | 126/91 R |
| 3,434,476 | 3/1969 | Shaw et al. | 128/303.1 |
| 3,662,755 | 5/1972 | Rautenbach et al. | 128/303 |
| 3,982,541 | 9/1976 | L'Esperance | 128/395 |
| 3,993,075 | 11/1976 | Lisenbee et al. | 128/303.1 |
| 4,022,214 | 5/1977 | Schulze et al. | 128/303.1 |
| 4,539,987 | 9/1985 | Nath et al. | 128/398 |
| 4,654,024 | 3/1987 | Crittenden et al. | 128/303.1 |
| 4,662,368 | 5/1987 | Hussein et al. | 128/398 |
| 4,669,467 | 1/1987 | Willett et al. | 128/303.1 |

FOREIGN PATENT DOCUMENTS

| | | | |
|---|---|---|---|
| 0007103 | 1/1980 | European Pat. Off. | 128/303.1 |
| 2826383 | 12/1979 | Fed. Rep. of Germany | 128/303.1 |

*Primary Examiner*—Max Hindenburg
*Attorney, Agent, or Firm*—Browdy and Neimark

[57] ABSTRACT

A catalytic thermal tip double catheter provides an alternative energy source for thermal angioplasty without the expense and technical support required for laser or electrical thermal angioplastic devices. The catalytic thermal tip catheter utilizes heat generated by the reactive of a stoichiometric ratio of oxygen and hydrogen gases catalyzed by a small piece of palladium sponge situated in a chamber adjacent to and enclosed by the metallic tip of the catheter, the vapors formed in the chamber generated being evacuated by a vacuum applied to an inner tube. Gas flow regulates catalytic thermal tip temperature which is monitored by a thermocouple positioned within the chamber. Vacuum and gas flow are controlled by an automatic or manual controller which is in direct communication with the temperature monitor.

15 Claims, 1 Drawing Sheet

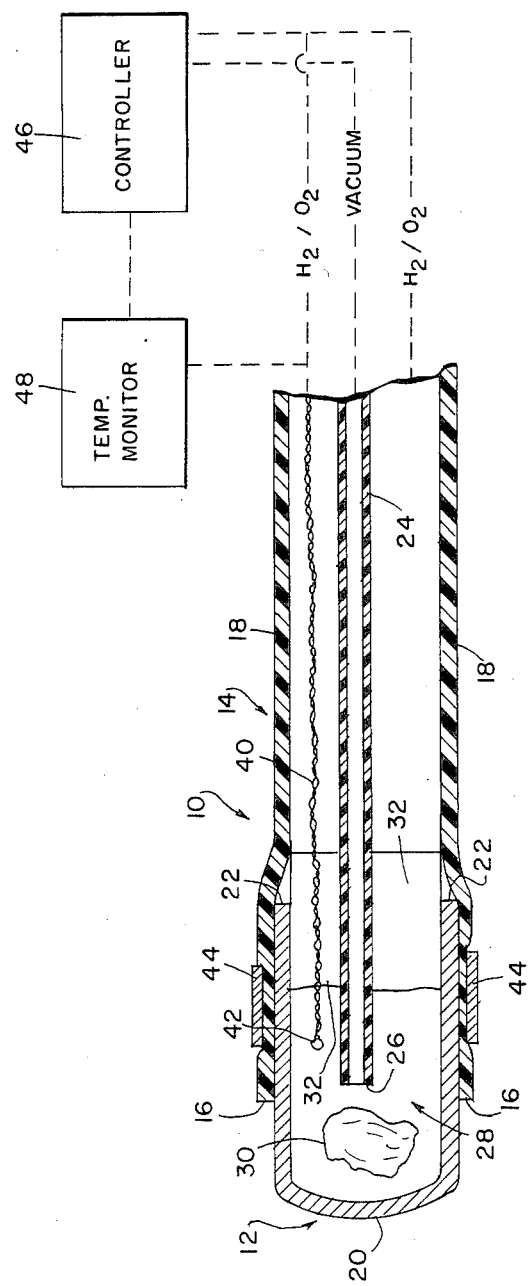

CATHETER WITH OXYHYDROGEN CATALYTIC THERMAL TIP

FIELD OF THE INVENTION

The present invention relates to thermal tip catheter surgical devices especially for performing thermal angioplasty including removing obstructed atherosclerotic lesions in arteries and ablating arrythmogenic foci in cardiac tissues, and for cacterization of bleeding vessels; and, more particularly, to thermal tip catheters utilizing catalytic reactions to thermally power or heat the catheter tip.

BACKGROUND OF THE INVENTION

Medical science, and especially the practice of angioplastic surgery, has experienced dramatic advances during the past several decades. More recently, the use of thermally-heated metallic tips for catheters has been suggested for ablating human atherosclerotic plaques and recanalizing obstructed low risk peripheral arteries. Those thermal tip catheters which have been so used require electrical or laser energy to heat the catheter tip to a desired temperature for carrying out the desired thermal surgery.

For example, experimental laser thermal angioplasty has been successfully performed in human peripheral arteries with low risks of vessel perforation (Sanborn et al, JACC 1985; 4:934-8), and preliminary studies regarding laser thermal angioplasty are ongoing in patients with coronary artery disease (Lancet 1986 II: 214-5; and Cumberland et al, Lancet 1986 I: 1457-9). In addition, electrical thermal tip catheters have also been designed and feasibility studies are being carried out (Lu et al, abstr. circ. 1986); these require about 10-15 watts for effective tissue ablation.

However, while electrical and laser thermal angioplasty has greatly improved, has achieved limited success and has some potential, the danger of exposing unnecessary electrical shock and other injuries to patients, particularly due to an electrical source or laser operating in a patient's blood vessels, is still a major undesired probability. Electrical and laser thermal angioplastic apparatus also have minimal control over the rate of tissue ablation due to lack of temperature monitoring of the working (distal) end or tip of the catheter.

Furthermore, when employing laser thermal angioplasty, a large technical and support staff are usually required to operate the laser apparatus effectively and safely. Moreover, laser system are necessarily cumbersome and nonportable, therefore restricting their practicality. Both the electrical and the laser thermal tip catheter systems are expensive to manufacture and require regular upkeep and maintenance to assure system operation and patient safety.

No thermal tip catheter or the like system has previously been available for successful angioplasty which does not require electrical or laser energy to heat the catheter tip. The need exists for a thermal tip angioplastic device which is safe, effective, less expensive, and easy to operate with minimal technical and support staff.

SUMMARY OF THE INVENTION

Accordingly, it is an object of the present invention to eliminate and overcome the deficiencies and disadvantages of the prior art, such as those set forth above.

It is another object of the invention to provide for improved, safer and less expensive angioplastic surgery.

It is a further object of the present invention to provide an improved thermal tip catheter for performing angioplasty and the like.

It is yet another object of the present invention to provide a thermal tip catheter which utilizes a catalytic exothermic reaction to heat the catheter tip.

It is yet a further object of the present invention to provide a thermal tip catheter system or the like for safely performing angioplasty or cauterization of bleeding vessels without the use of electrical or laser energy.

It is still another object of the present invention to provide a catalytic thermal tip catheter which is simple and inexpensive to manufacturer and to use in surgery.

It is still a further object of the present invention to provide a catalytic thermal tip catheter which is lightweight and portable and which will not require a large technical and support staff to safely operate the same.

Other objects of the present invention are to provide a catalytic thermal tip catheter employing a temperature monitoring capability to monitor the heat generated during catalytic reactions; to provide a catalytic thermal tip catheter including a vacuum disposal system; and to provide a catalytic thermal tip catheter system which will guide the rate of tissue ablation and avoid vessel wall perforation during angioplasty through the utilization of a monitoring/controlling system.

Still other objects, features and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWING

The single FIGURE shows a partial cross-sectional view of the catalytic thermal tip catheter of the present invention, particularly illustrating the working end of the catheter.

DESCRIPTION OF THE PREFERRED EMBODIMENT

A preferred embodiment 10 of the present invention is schematically illustrated in the sole FIGURE, and includes a catheter body 14 provided with a catalytic tip 12 at its working end. The body 14 of the catheter 10 includes an outer tubing 18 having a distal end 16 which is slid over the proximal open end 22 of a thin-walled metallic tip 20 which defines the thermal tip 12 with a chamber 28 therewithin. An inner tubing 24 is coaxially mounted within the outer tubing 18, the inner tubing having an open distal end 26 positioned at a fixed distance from the metallic tip 20. Within the chamber 28 between the metallic tip 20 and the end 26 of the tubing 24 is located a suitable catalyst, such as a palladium sponge 30.

The metallic tip 20 is desirably formed of surgical grade stainless steel, although other inert metals or even non-metallic materials of good heat resistance and heat conductivity could be used. Tubing 18 and 24 of the catheter 10 is preferably formed of Teflon, i.e. polytetrafluroethylene but other inert and heat resistant materials can be used as long as the tubing is of a diameter to permit invasive passage of the catheter through blood vessels and arteries, and if the material under those conditions is sufficiently rigid so as to maintain a circular cross-section while being sufficiently flexible to properly function as a blood vessel catheter. For example, polyimides and certain heat resistant silicone resins can be used instead of Teflon.

Inner tubing 24, near its distal open end 26, is supported by any suitable means such as an annular through-hole collar or the like for securing the tubing distal end 26 at a fixed distance from the interior surface of the metallic tip 20. In the illustrated embodiment, spacing is provided simply by the welding of two axially extending pins, rods or wires 32 to the inner surface of the metallic tip 20 near its proximal end 22, the wires 32 being spaced roughly 180° from one another. Regardless of the spacer used, axial through-openings must be provided to permit passage of reactive gases from the proximal end of the catheter 10 to the reaction cavity 28 at the distal end 12 downstream of the spacer. It is also desirable to mount a temperature monitoring thermocouple 40 or the like having a sensor 42 at its end, the thermocouple 40 passing through such a through-opening and the sensor 42 being positioned within the reaction cavity 28. The inner tubing 24 provides a conduct for applying a vacuum from the proximal end to the reaction cavity 28, particularly employed to dispose of gases and vapors generated during catalytic reactions carried out in the catalytic chamber 28.

The metallic tip 20 is connected to the open distal end of the outer tubing 18 as shown and described above, and is annularly sealed via a metal ring constrictor 44 which provides a tight fluid seal during operation at high temperatures. Due to the high coefficient of heat of expansion of Teflon, the seal 44 becomes tighter as the tip 20 is heated and expansion occurs. The metallic tip 20 is extremely small having a diameter of approximately 0.9 mm, and it will be consequently understood that all the parts are small and the drawing is on an enlarged scale.

The device of the present invention utilizes the combustion of oxygen and hydrogen reactive gases as the energy source to heat the metallic tip 20. Oxygen and hydrogen gases are suitably generated near the proximal end of the device using typical electrolytic processes; alternatively, the gases may be made elsewhere and stored, although this option is less safe. Regardless, a stoichiometric ratio of oxyhydrogen is passed down the annular space of the catheter 10 between the outer tubing 18 and the inner tubing 24. The amount of gases delivered to the annular space may be controlled by a manual or automatic controller 46 which is in direct communication with a temperature monitoring system 48, the monitoring system being connected to the thermocouple assembly 40.

In operation, the oxyhydrogen gas reaches the catalytic chamber 28, encased by the metallic tip 20, where a piece of palladium sponge 30 resides, and chemical combustion is started by the catalytic action of the palladium sponge on the mixture of oxygen and hydrogen. For every two milli-moles of hydrogen gas ($H_2$) and one milli-mole of oxygen gas ($O_2$) consumed, 136 calories or 568 joules of energy in form of heat are delivered to the metallic tip 20 and by conduction through the metallic tip 20 to the locus of surgery. It will of course be understood that the reaction takes place on the surface of the catalyst and therefore where the catalyst contacts the interior of the metallic tip 20 the heat will be conducted directly therefrom to and through the metallic tip 20. The water vapor or steam formed within the chamber 28 by the reaction of $H_2$ and $O_2$ is evacuated through the inner tubing 25 by means of a vacuum applied to its distal end 26 from its proximal end. This vacuum may also be regulated by the controller 46. Without evacuating the formed steam rapidly, the water vapor condenses to form liquid water which may wet and inhibit the catalytic activity of the palladium sponge 30, thus making it difficult to later reinitiate the chemical combustion of the hydrogen.

The double catheter system gives the added advantage to the well-known countercurrent heat exchange system. The oxyhydrogen passing down the annular space between the outer tubing 18 and the inner tubing 24 is progressively heated by the high temperature steam that is evacuated through the inner tubing 24. Increased efficiency of combustion of the hydrogen is thus achieved, and the heat of the water vapor is dissipated to the incoming gases and not to the surrounding tissue along the length of the catheter body 14.

The amount of heating of the metallic tip 20 is regulated easily by the amount of oxyhydrogen delivered through the catheter, via controller 46. The thermocoupled sensor 42 placed or positioned within the catalytic chamber 28 provides a feedback signal to control the amount of gas delivered. The controller 46 regulates the amount of heating and minimizes any unwanted tissue injury.

It should be understood that due to moisture absorbed by the palladium sponge which temporarily destroys its catalytic activity, the device needs to be heat activated initially to dry the palladium sponge prior to operation. Heat activation is performed simply by heating the metallic tip with either a heating gun (e.g., a hair dryer), hot plate, or gas flame to approximately 80° C. Once activated, the device can operate without reactivation even if the oxyhydrogen gas has been turned off for 10–15 minutes. In addition, reactivation is never a problem if the metallic tip temperature is maintained above 35°–40° C.

It should be understood that other catalytic materials for the sponge may be employed. For example, a platinum sponge may be used, as opposed to a palladium sponge, to react with the oxyhydrogen gas. Furthermore, reactive gases other than oxygen and hydrogen may be employed to react with a catalyst situated in the catalytic chamber.

By way of example, a catheter 10 as described above was studied in air and saline, alone and with human atherosclerotic aortic segments. Heating was faster in air (>350° C. in <1 sec.) than saline (Temp. (max) of 170° C. in 5 sec., $t_{\frac{1}{2}}$=0.6 sec.), but thermal relaxation was faster in saline ($t_{\frac{1}{2}}$=1.5 sec.) than air ($t_{\frac{1}{2}}$=8 sec.) due to rapid heat convection in saline. In both air and saline, catalytic thermal tip-tissue contact effects were directly related to temperature at the tip; histologic thermal injury began at Temp.>180° C. but ablation with crater formation, charring, and polymorphous vacuoles did ont occur until Temp. >325° C. Effective tissue ablation in saline required initial vaporization of the saline at the catalytic thermal tip-tissue interface.

It was conducted that the catalytic thermal tip catheter is safe, inexpensive, and results in efficacious tissue ablation which can be easily and effectively regulated by temperature feedback monitoring, and therefore the present invention is an apparent and excellent alternative to laser and electrical thermal angioplasty.

It will be obvious to those skilled in the art that various other changes and modifications may be made without departing from the scope of the invention and the invention is not to be considered limited to what is shown in the drawing and described in the specifications.

What is claimed is:

1. A catalytic thermal tip catheter, comprising: a distal metallic tip end; a catalytic chamber adjacent to and partially enclosed by said metallic tip; a catalyst for initiating an exothermic reaction between two gases, located in said chamber; and elongated catheter body comprising means for the passage of a reactive gas from a remote location to said catalytic chamber; whereby introduction of said reactive gas in said catalytic chamber effects a catalytically initiated chemical reaction which produces heat conducted directly to said metallic tip to heat said metallic tip to a temperature of at least 180° C.

2. A catheter in accordance with claim 1, further including a thermocouple situated in said chamber to monitor the temperature of said catalytic reaction in said chamber.

3. A catheter in accordance with claim 1, further including gas removal and heat exchange means for evacuating reaction gases generated by said chemical reaction and for pre-heating incoming gases and cooling reaction gases, comprising an inner tubing within said catheter body and in communication with said chamber.

4. A catheter in accordance with claim 3, wherein said means for evacuating reaction gases further comprises means for applying a vacuum to said inner tubing.

5. A catheter in accordance with claim 1, further comprising control means for regulating passage of reactive gases to said chamber.

6. A catheter in accordance with claim 1, wherein said catalyst is a catalyst for effecting chemical combustion between oxygen and a combustible gas.

7. A catheter in accordance with claim 1, wherein said means for the passage of reactive gas further comprises means for feeding a stoichiometric ratio of oxygen and hydrogen gases.

8. A catheter in accordance with claim 7, wherein said catalyst in said chamber is a palladium sponge.

9. A catalytically heated thermal tip catheter, comprising:
an outer catheter tube having a thin-walled metallic tip at its distal end; an inner tube mounted within said outer catheter tube, said inner tube having an open distal end positioned at a fixed distance from said metallic tip; positioning means for mounting said inner tube at a fixed position within said outer tube and including through-holes for the passage of reactive gases past said positioning means; a catalytic reaction chamber defined by and within said metallic tip and into which the open distal end of said inner tube projects; a catalyst for initiating reaction between $O_2$ and $H_2$ situated in said chamber; and means for the passage of $O_2$ and $H_2$ to said chamber through a generally annular space formed between said inner tube and said outer tube for reacting in said chamber by the action of said catalyst to effect reaction and provide sufficient heat to said metallic tip to heat said tip to at least 180° C.

10. A catheter in accordance with claim 9, wherein said metallic tip and the distal end of said outer tube are sealed with an annular metal ring constrictor.

11. A catheter in accordance with claim 9, further including temperature monitoring means for monitoring the temperature within said catalytic chamber.

12. A catheter in accordance with claim 11, wherein said temperature monitoring means includes a thermocouple.

13. A catheter in accordance with claim 9, further including a controller for regulating said passage of reactive gases.

14. A catheter in accordance with claim 9, further comprising means for applying vacuum to said inner tube to evacuate vapor generated in said catalytic chamber.

15. A catheter in accordance with claim 9, wherein said outer tubing is polytetrafluroethylene.

* * * * *

UNITED STATES PATENT AND TRADEMARK OFFICE
CERTIFICATE OF CORRECTION

PATENT NO. : 4,796,622

DATED : January 10, 1989

INVENTOR(S) : Lu et al.

It is certified that error appears in the above-identified patent and that said Letters Patent is hereby corrected as shown below:

| | |
|---|---|
| Column 2, line 47 | After the word "catalytic", insert the word --thermal-- |
| Column 4, line 1 | Delete "25" and insert therefor --24-- |
| Column 4, line 10 | Delete "to" and insert therefor --of-- |
| Column 4, line 57 | Delete "ont" and insert therefor --not-- |
| Column 5, line 9 | Delete "and" and insert therefor --an-- |

Signed and Sealed this

Twenty-second Day of October, 1991

Attest:

HARRY F. MANBECK, JR.

Attesting Officer

Commissioner of Patents and Trademarks